US009808187B2

(12) United States Patent
Freitag

(10) Patent No.: US 9,808,187 B2
(45) Date of Patent: Nov. 7, 2017

(54) MEASURING CHAMBER FOR AN OPTICAL SENSOR FOR DETERMINING A CONCENTRATION OF A SUBSTANCE IN THE TISSUE FLUID OF A MAMMAL

(71) Applicant: Schildtec GmbH, Erfurt (DE)

(72) Inventor: Hans-Joachim Freitag, Erfurt (DE)

(73) Assignee: Schildtec GMBH, Erfurt (DE)

( * ) Notice: Subject to any disclaimer, the term of this patent is extended or adjusted under 35 U.S.C. 154(b) by 110 days.

(21) Appl. No.: 14/362,365

(22) PCT Filed: Nov. 30, 2012

(86) PCT No.: PCT/EP2012/074168
§ 371 (c)(1),
(2) Date: Aug. 1, 2014

(87) PCT Pub. No.: WO2013/079704
PCT Pub. Date: Jun. 6, 2013

(65) Prior Publication Data
US 2014/0350363 A1    Nov. 27, 2014

(30) Foreign Application Priority Data

Dec. 2, 2011  (DE) .................... 10 2011 087 679

(51) Int. Cl.
*A61B 5/1455*  (2006.01)
*A61B 5/145*   (2006.01)
(Continued)

(52) U.S. Cl.
CPC ........ *A61B 5/14514* (2013.01); *A61B 5/1451* (2013.01); *A61B 5/1459* (2013.01);
(Continued)

(58) Field of Classification Search
CPC .............. A61B 5/1455; A61B 5/14552; A61B 5/14532; A61B 5/0059; A61B 5/6826
See application file for complete search history.

(56) References Cited

U.S. PATENT DOCUMENTS 5,365,925 A * 11/1994 Lee ...................... A61B 5/1495
356/243.1
5,997,501 A * 12/1999 Gross ................ A61M 5/14248
604/65
(Continued)

FOREIGN PATENT DOCUMENTS

CN      1987024 A     6/2007
CN    101036575 A     9/2007
(Continued)

*Primary Examiner* — Erik Winakur
*Assistant Examiner* — Marjan Fardanesh
(74) *Attorney, Agent, or Firm* — Patterson Thuente Pedersen, P.A.

(57) ABSTRACT

A measuring chamber device for an optically operating sensor for determining a concentration of a substance that is contained in tissue fluid of a mammal. The measuring chamber device has a measuring chamber filled with a liquid measuring medium and a wall with better diffusion permeability for the substance than for other constituents of the tissue fluid. A transmitter device for emitting optical radiation into the measuring chamber, and a receiver device for receiving optical radiation that has passed through the measuring chamber are also provided.

22 Claims, 7 Drawing Sheets

Figure 1:
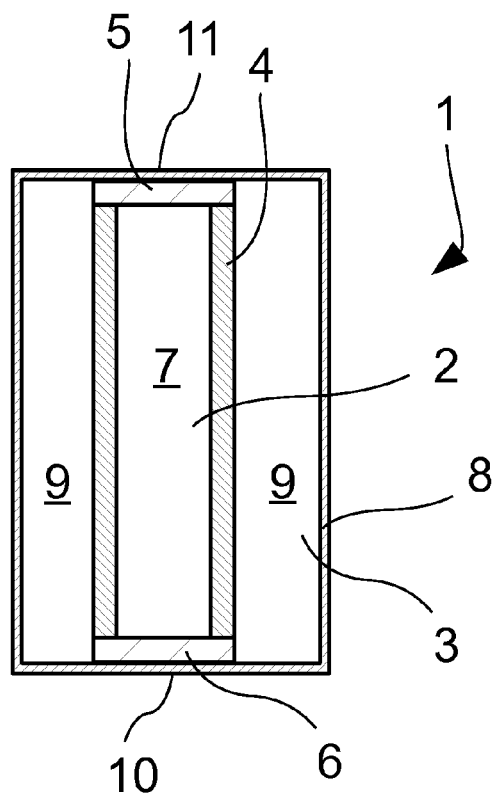

(51) Int. Cl.
  *A61B 5/1459* (2006.01)
  *A61B 5/1495* (2006.01)
  *G01N 21/03* (2006.01)
  *G01N 21/27* (2006.01)

(52) U.S. Cl.
  CPC ........ *A61B 5/1495* (2013.01); *A61B 5/14532* (2013.01); *A61B 5/14558* (2013.01); *G01N 21/03* (2013.01); *G01N 21/274* (2013.01); *G01N 2021/0346* (2013.01); *G01N 2021/0385* (2013.01); *G01N 2021/0392* (2013.01); *Y10T 29/49826* (2015.01)

(56) References Cited

U.S. PATENT DOCUMENTS

| | | | | |
|---|---|---|---|---|
| 5,997,811 A * | 12/1999 | Esposito | ............ | A61B 10/0096 422/1 |
| 6,214,560 B1 * | 4/2001 | Yguerabide | ......... | C12Q 1/6816 422/50 |
| 7,738,934 B2 | 6/2010 | Takase et al. | | |
| 8,141,409 B2 | 3/2012 | Crane et al. | | |
| 9,097,687 B2 | 8/2015 | Crane et al. | | |
| 2003/0050542 A1 * | 3/2003 | Reihl | ................... | A61B 5/1459 600/316 |
| 2004/0120848 A1 * | 6/2004 | Teodorczyk | .......... | A61L 2/0011 422/22 |
| 2005/0158205 A1 * | 7/2005 | Swanson | ............ | A61B 5/1486 422/22 |
| 2007/0219436 A1 | 9/2007 | Takase et al. | | |
| 2008/0249435 A1 | 10/2008 | Haar et al. | | |
| 2009/0145788 A1 * | 6/2009 | Doshi | ....................... | B26F 1/02 206/370 |
| 2009/0257911 A1 * | 10/2009 | Thomas | ............. | A61B 5/14532 422/22 |
| 2009/0277242 A1 * | 11/2009 | Crane | ................ | A61B 5/14546 73/1.02 |
| 2010/0134798 A1 * | 6/2010 | Zirk | ................... | A61B 5/14532 356/367 |
| 2010/0249558 A1 * | 9/2010 | Yodfat | ............. | A61M 5/14248 600/345 |
| 2011/0118570 A1 | 5/2011 | Pedersen | | |
| 2011/0270113 A1 * | 11/2011 | Heyne | ................ | A61B 5/0836 600/531 |
| 2012/0240656 A1 | 9/2012 | Crane et al. | | |
| 2013/0345597 A1 | 12/2013 | Hagino et al. | | |

FOREIGN PATENT DOCUMENTS

| | | |
|---|---|---|
| CN | 101287406 A | 10/2008 |
| CN | 101819136 A | 9/2010 |
| CN | 101987024 A | 3/2011 |
| DE | 3736092 A1 | 5/1989 |
| DE | 19911265 A1 | 9/2000 |
| DE | 103 21 356 A1 | 12/2004 |
| DE | 10 2007 031284 A1 | 1/2009 |
| EP | 0638280 A1 | 2/1995 |
| EP | 2041562 A1 | 4/2009 |
| WO | WO 99/53296 A1 | 10/1999 |
| WO | WO 2009/015723 A1 | 2/2009 |
| WO | WO 2009/066287 A2 | 5/2009 |
| WO | WO 2009/121360 A1 | 10/2009 |

* cited by examiner

MEASURING CHAMBER FOR AN OPTICAL SENSOR FOR DETERMINING A CONCENTRATION OF A SUBSTANCE IN THE TISSUE FLUID OF A MAMMAL

RELATED APPLICATIONS

The present application is a National Phase entry of PCT Application No. PCT/EP2012/074168, filed Nov. 30, 2012, which claims priority from DE Application No. 10 2011 087 679.0, filed Dec. 2, 2011, said applications being hereby fully incorporated herein by reference in their entirety.

FIELD OF THE INVENTION

The invention relates to a measurement chamber device for an optical sensor for determining the concentration of a substance, which is present in the interstitial fluid of a mammal, wherein the measurement chamber device comprises a measurement chamber which is designed to be inserted into the body of the mammal, which is filled with a measurement fluid and which comprises a wall, which enables at least in a wall section a better diffusion of the substance than for other components of the interstitial fluid.

The invention relates further to a module for a substance concentration measuring sensor, which module comprises a measurement chamber device of the type above.

The invention relates further to a substance concentration measuring sensor which comprises a measurement chamber device of the type above.

The invention relates further to a manufacturing process for said measurement chamber device, for said module or for said sensor.

BACKGROUND OF THE INVENTION

Measuring a concentration of a substance is a common technical task. This task is particular challenging, if the substance under investigation is contained in a mixture of different substances. Such a matrix requires a measurement principle not only of high sensitivity, but also of high selectivity to obtain a good measurement of concentration. Often, a single measurement is not sufficient and costly selection procedure, for instance gas chromatography etc., must be utilized. The difficulty of the measurement task increases with the complexity of the matrix.

Very complex substance mixtures are usually be found in biology. For this reason, measurement of a concentration of a substance in a biological matrix is one of the most challenging tasks.

Generally, there is a clear trade-off between the measurement complexity and the options to miniaturize a measurement system. However, miniaturized sensor systems are very attractive for biological applications. It is well known, that a well regulated concentration of certain substances such as glucose, sodium chloride, uric acid, amino acid, etc. is vital for humans. In case of a disease the biological regulation of the concentration can misalign and the concentration of one or more vital substances can be outside the physiologically harmless range. To avoid such disturbance through therapeutic treatment requires to know the current concentration of the substances under investigation; thus, the concentration must be measured, sometimes continuously. Single use test strips are not suitable, then.

For instance diabetes mellitus, caused by a disturbed regulation of the metabolism of glucose in the body, is causing too high (hyperglycenic) or too low (hypoglycenic) concentrations. In the long term, this causes irreversible dieback of nerve cells and a set of further diseases mainly of blood vessels. Resulting diseases can be blindness, loss of renal function, cardiac infarction, high blood pressure and the dieback of extremities. The therapy of diabetes requires an adjustment of the glucose level on a permanent base within the harmless medial range as precisely as possible, e. g. by administering insulin or glucose. Schedule and volume of insulin injections or the need to take food depend on the current glucose concentration as well as the concentration change during the day.

The concentration of glucose is, therefore, an example for a measurement task of a substance concentration in a complex matrix, which is to be monitored continuously without interruption and without extensive repetitive adjustments. All treatments and therapies today are based on influencing the blood glucose level. This is the reason why most glucose concentration measurement devices measure the glucose concentration in the blood. In is also known, to utilize the interstitial fluid, since its glucose content follows the concentration in blood with only a small time delay.

E.g. DE 19911265 C2 describes a device for measuring the concentration of glucose in protein-containing aqueous solutions, in particular in the interstitial tissue fluid, where a dialysis extract is characterized polarimetrically and spectroscopic at the same time. The parallel application of two measurement techniques causes a significant complexity and expenditure. The described solution results in an expected large technical construction. In addition a plasite dialysis membrane for the separation of substances is required, while the challenging technical coupling of this membrane to the optical measurement system is not described in detail.

A similar approach is described in DE 3736092 A1.

When measuring the concentration of the substance in a biological tissue, the tissue or the interstitial fluid forms a matrix. To address this issue, a sensor is required which can be inserted into the tissue to enable a permanent observation of the substance concentration. Such sensor is known from DE 102007031284 A1. This apparatus realizes measurement chamber, optical transmitter and receiver as a compact unit, which can be inserted into the body of a mammal.

To insert into the body of a mammal requires a reliable sterilization of the sensor. The apparatus of DE 102007031284 A1 requires also sterilization of the measuring fluid enclosed in the sensor. This can be done only by the application of ionizing (radioactive) radiation, which involves the issue of damage of the transmitter and of the receiver from the ionizing radiation.

Manufacturing the sensor according to DE 102007031284 A1 requires to fill of the measurement chamber without any bubbles, which requires the use of vacuum for ensuring process reliability. At the same time, this requires that the whole sensor is immersed within the measurement fluid. In such vacuum assisted filling one must take care that transmitter and receiver and in particular their optical components are not filled with the measurement fluid. This involves a significant effort to protect these elements.

The measurement chamber wall used in the sensor concept according to DE 102007031284 A1 allows diffusion for the measurement fluid or at least a part thereof. To avoid evaporation or leakage of the measurement fluid, this approach stores the sensor in a storage container topped up with the measurement fluid. In case of glucose measurement, the storage container is filled with saline solution which is the measurement fluid. Such storage results in demanding specifications and high manufacturing costs to protect optical and electronic components of the sensors. All electric connections and wiring need to be protected against corrosion caused by the saline solution. Storage in the storage container filled with saline solution imposes furthermore a large risk for the long term stability and heavily reduces for the maximum shelf life of the sensor.

SUMMARY OF THE INVENTION

This invention addresses the problem to simplify the concept of DE 102007031284 A1 as regards to storage and manufacturing.

This problem is solved by a measurement chamber device for an optical sensor for measuring a concentration of a substance being part of an interstitial fluid of a mammal, wherein the measurement chamber device comprises a measurement chamber, which is adapted to be inserted into the body of the mammal, is filled with a measurement fluid and comprises a wall, which comprises at least one wall section enabling a better diffusion of the substance than of other components of the interstitial fluid, wherein the measurement chamber comprises a first measurement chamber window section designed to be connected to a transmitter unit for emitting optical radiation into the measurement chamber and a second measurement chamber window section designed to be connected to a receiver unit for detecting optical radiation transmitted through the measurement chamber, wherein the wall and the measurement window sections enclose the measurement fluid leakproof, and wherein the measurement chamber device comprises a sterilization envelope, which encloses the wall section of the measurement chamber, but not the transmitter unit and the receiver unit and does not block the optical radiation at the measurement chamber window sections, wherein the sterilization envelope is filled also with measurement fluid to bath the wall section in measurement fluid and is removable before use of the measurement chamber.

The problem is further solved by a module for a substance concentration measuring sensor, which module is characterized by a measurement chamber device according to the above claims, wherein the first measurement chamber window section is located opposite the second measurement chamber window section and wherein the measurement chamber is adapted for transmission of the optical radiation without reflections.

The problem is furthermore solved by a substance concentration measuring sensor, which is characterized by a measurement chamber device according to the above claims with a transmitter attached to the first measurement chamber windows section and a receiver attached to the second measurement chamber window section.

The problem is equally solved by a technical process for manufacturing the measurement chamber device of to the invention, wherein a) the measurement chamber is enclosed by the sterilization envelope which includes a port, b) the unit of the measurement chamber and the sterilization envelope is filled with the measurement fluid under vacuum conditions and the port is closed and c) the filled unit is sterilized by utilizing ionizing radiation.

The concept according to the invention provides an independent measurement chamber device, which is later, in particular at the time of application at the patient, completed by the transmitter unit and the receiver unit to obtain the final sensor. Such modular construction is, according to the invention, achieved in that the measurement chamber comprises the measurement chamber window sections and confines the measurement fluid. For a simple sterilization and for simplifying storage of the measurement chamber device, the measurement chamber is covered by the sterilization envelope at least in the regions of the diffusion permeable wall section, which envelope is also filled with the measurement fluid. This ensures that the measurement fluid can not leak, e.g. evaporate, from the measurement chamber during storage. At the same time, the measurement chamber device can be sterilized in a very simple way by ionizing radiation, because the radiation sensitive transmitter and receiver units can be mounted later after the sterilization procedure. It is also possible to fill the measurement chamber including the sterilization envelope, without transmitter unit and receiver unit being installed, i. e. without a need to protect these parts at filling.

After being filled and sterilized by ionizing radiation, the measurement chamber can be completed by the transmitter unit and/or the receiver unit in a simple way. The module or the complete sensor assembled in this way can be surface sterilized without problems, for instance by chemical sterilization, because the filling of the measurement chamber and of the sterilization envelope is already aseptic due to the preceding ionizing radiation process.

The modular structure of measurement chamber device, transmitter unit and receiver unit enables a finalization to different degrees. It is possible to complete the sterilized measurement chamber device after being sterilized by ionizing radiation by the transmitter and receiver units and to surface-sterilize the whole device even at the production site. This gives a sterilized sensor, which requires only to remove the sterilization envelope before insertion in the body.

A lower degree of finalization is equally possible. It turned out, that components of a sensor which have been inserted into the body of a mammal must be replaced after a certain period of application. This affects in any case the measurement chamber and, depending on the design, also the transmitter unit. Therefore, it is possible without problems to provide such consumable module separately. The measurement chamber device, which is sterilized by ionizing radiation, can easily be completed by the transmitter unit and provided as a module. This module is replaced by separating the module to be replaced from the receiver unit and substituted by a fresh module. It is not necessary to replace the receiver unit.

It is an essential feature of the concept according to the invention that the measurement chamber is realized such, that its wall and the measurement chamber window sections, which are prepared for a connection to the transmitter and receiver units, are enclosing the measuring fluid leak proof. The sterilization envelope encloses at least the diffusion permeable wall of the measurement chamber, but does not block the measurement chamber window sections for optical radiation and does also not enclose the transmitter and receiver units. Therefore, transmitter unit and receiver unit can be mounted to the measurement window sections, while the sterilization envelope (still) encloses the measurement chamber.

The sterilization envelope can be attached sealingly to those sections of the measurement chamber, which surround the measurement chamber window sections. Then, the sterilization envelope does not cover the measurement window sections. The section to which the sterilization envelope is attached may be appropriate cavities, recesses and notches at the measurement chamber window sections. A possible example is a step-like collar at the respective measurement chamber window sections, to which an edge of the sterilization envelope is attached.

Using an optical transparent sterilization envelope, which fully encloses also the measurement camber window sections and overlaps with the measurement chamber window sections, may be an alternative to keeping the measurement chamber window sections uncovered. In such overlap area the sterilization envelope remains at the sensor, even after the transmitter and the receiver units have been mounted to the measurement chamber window sections. It is not required to have transparency end-to-end. Transparent window sections in the envelope wall are sufficient.

The envelope wall of the sterilization envelope can simply be realized by using a foil, which is ripped off to remove the sterilization envelope. Pull strips can be provided for this purpose.

The measurement chamber window sections and the wall enclose the measurement fluid inside the chamber leak proof. This requires a suitable bond between the measurement chamber window sections and the wall. An adhesive bond can be used. However, a gluing process could reduce the diffusion permeability of the wall at least in the gluing area, because the adhesive penetrates the wall. Areas of reduced diffusion permeability are usually found near the contact of measurement chamber window section and wall. To avoid such areas corrupting the measurement, it is preferred that the measurement window sections protrude into the measurement chamber and overlap those areas. Then, these areas do not participate in diffusion. Any change of the diffusion properties in those areas does result in a measurement error, thus.

The mounting of the transmitter unit and/or receiver unit at the measurement chamber window sections can be realized by different technologies, for instance adhesive bonding. In view of the modular use of the measurement chamber device, a mounting of transmitter unit or receiver unit which also offers a precise positioning is preferred. This can be realized for instance by combining adhesive bonding or cementing with suitable adjusting structure. It is also possible to use a flange for mounting the transmitter and receiver units.

Mounting of the transmitter and receiver units to the measurement chamber window sections has to be done such that optical radiation can be coupled in and out to the measurement chamber window sections. Beside an adhesive bonding or cementing which fulfills the optical requirements, it is also possible to provide an immersion fluid reservoir to ensure transmission of optical radiation through the interface. This can be used for the mounting of the transmitter unit and/or the receiver unit.

Transmitter and/or receiver can also be connected by an optical fiber. If polarization is to be detected, a single-mode fiber which maintains polarization is used. When connecting transmitter and/or receiver by the optical fiber it is preferred to provide the corresponding measurement chamber window section(s) in form of fiber coupler(s). To use a fiber coupled transmitter and/or receiver has the advantage of simplified sterilization requirements. Furthermore, the location of transmitter and receiver becomes flexible. Therefore, the term "window section" includes coupler embodiments as well.

As known from the state of the art, a sensor should be calibrated before use, wherein a two-point calibration is preferred. To improve shelf-life of the sensor, it is of advantage to calibrate directly before application of the issue. A two-point calibration requires that the measurement chamber is filled with two measurement fluids in sequence, wherein the fluids are different in composition, in particular in concentration of the substance under investigation, e. g.
glucose. Therefore, it is preferred to connect the sterilization envelope of the measurement chamber to a calibration chamber via a fluid duct, wherein the calibration chamber contains a calibration fluid. The fluid duct can be opened to mix the calibration fluid with the measurement fluid for calibration purposes. This allows to realize two measurement points for calibration. A first calibration point is realized by using the measurement fluid which was pre-filled to the measurement chamber during production. The second calibration point is realized by fluidically connecting the measurement chamber with the calibration camber, e. g. by opening an already existing fluid duct. Then, the calibration fluid and the measurement fluid admix. The mixture is used to create a second measurement point. The relation of the volumes of measurement chamber and calibration chamber and the corresponding concentrations are, of course, relevant to calibration.

The mounting of a sensor which is incorporated in the body of a mammal is, of course, of particular importance, if parts of the sensor are still outside the body. This is the case for the inventive sensor concept, because the measurement chamber is usually inside the body of the mammal and the receiver unit and the electronics for data processing are outside the mammal's body. A gentle way of position fixation is to provide a flexible support structure, which can be attached to the skin of the mammal, for instance a form of a collar. This supports the parts which are penetrating the mammal's body in flexible manner so that these parts can follow any body movements etc.

Advantageously a cover which is attached to the skin of the mammal of independently to the measurement chamber is provided over the part of the sensor which protrudes outside the body, usually the receiver unit. Any contact, pressure or other force to the protection cover does not cause a painful movement of the very parts, which penetrate the body, because there is no rigid connection between the protection cover and any part of the sensor, which is inside the body or which is connected to parts inside the body.

To ensure operation of the measurement chamber device, the volume of the measurement chamber should be filled as bubble-free as possible. To tolerate any small remaining bubbles in the measurement chamber, it is of advantage to have a convex surface at the interior face of at least one of the measurement chamber window sections. Such a convex surface pushes small residual bubbles to the side of the window section such that they disturb optical transmission through the measurement chamber not or as less as possible. In general it is sufficient to have a convex window surface which is at the top end during the application of the sensor system, since any small remaining bubbles will rise to the top. If the later orientation of the measurement chamber is not defined, it is preferred to provide both measurement chamber window sections convex at their inside faces. Such convex construction can be an advantage independently of the sterilization envelope.

Due to the difference in the refraction index between the material of the measurement chamber window sections and the fluid, those convex surfaces can in addition be used as optical surfaces for optical beam forming or to avoid disturbing edge effects. This gives a better focusing of the light beam or avoids any interfering edge effects.

The measurement chamber device can be finalized to form a module for a substance concentration measuring sensor, which is ready for insertion into the body of the mammal, by connecting the transmission unit to the first measurement chamber window section. In case the measurement chamber is designed for a single transmission of an optical beam, e.g. in case first and second measurement chamber window sections are on opposing ends of the measurement chamber, such module comprises all components which are inside the mammal's body. This construction is in general preferred, because it results in a slim module. On the other hand, an option is possible which provides an optically reflecting element in the measurement chamber to enable a realization with first and second measurement chamber window sections not on opposing sides, but e.g. in a side-by-side configuration. This has the advantage that the transmitter and receiver units can both remain outside the mammal's body, in particular can be combined into a single transmitter-receiver unit.

To eliminate optical disturbances, it is of advantage to use protection covers and/or flexible support structures made from optically not transparent material.

According to the concept of the invention, at least the measurement chamber and preferred the module described above is pierced into the mammal's body. The measurement chamber is preferred to be located under the skin completely. This can be realized most easily by a penetration which is almost perpendicular with respect to the skin. To avoid any injury of organs and blood vessels, a tilted penetration is of an advantage. To ensure even in this case, that the measurement chamber is fully located below the skin, e.g. is completely inside the body of the mammal, it is preferred to provide an extension for the measurement chamber window section(s) to which the transmitter and/or receiver unit are connected which remains outside the mammal's body. This enables a complete penetration to the body even at tilted piercing angles.

By diffusion separation of the substance from the matrix (interstitial fluid) the sensor principle resolves the known low specificity problem of pure physical methods of the state of the art. By diffusion driven separation of the substance from the matrix the sensor can realize a simple optical measurement and is, thus, quite compact. Due to particular diffusion properties the wall separates the substance under investigation from the matrix and increases the concentration of the substance within the measurement chamber, by separating the substance under investigation from the other matrix components. The diffusion separation can be realized by a size-depended and/or a shape-depended selection process; this means the wall gives passage only for molecules of a certain range of size or shape.

Due to the separation by diffusion of the sensor, the optical measurement method is significantly simplified, which results in a compact, miniaturized and cost-efficient realization. In particular the separation by diffusion prevents certain substances from entering the measurement chamber to which substances the measurement method may be much more sensitive than to the substance under investigation.

The electromagnetic optical measurement beam produced by the transmitter unit (for instance of a wavelength between 0.8 and 1.5 μm) passes through the measurement fluid. By providing the measurement beam with certain polarization states (unpolarized, partial polarized, linear polarized, elliptic polarized or circular polarized) and/or spectral composition it is possible define the measurement method (polarimetry, absorption or stray-light) and, thus, tune the sensor to one or several substances. Having passed the measurement fluid, the measurement beam hits the receiver unit, which comprises at least two independent detectors behind a beam splitter. This allows for an extensive analysis of the measurement beam. In case the receiver is located opposite the transmitter only a single pass through the measurement fluid is required, and the apparatus is slim.

The diffusion properties of the wall are designed such that a good diffusion and transport is possible only for the substance under investigation, but not for other substances present in the matrix. In embodiments of the invention the diffusion properties of the wall are specifically selected or designed with respect to the matrix and the substance.

The diffusion properties of the wall provide for the desired selectivity of the sensor, such that the optical measurement in the measurement chamber has a high specific accuracy and a low detection limit for the substance, without the requirement of complex optical systems. Moreover, the diffusion selection makes a long measurement channel unnecessary, which results in a very compact set-up.

Preferably, the measurement chamber device comprises a elongated housing, for instance a capillary tube, to the ends of which the measurement chamber window sections are attached. The cross section of the elongated housing has no relation to the measurement accuracy, whereby a slim housing, for instance with a diameter below 3 mm, operating as a piercing probe can be realized.

The optical measurement in the measurement chamber is selected according to the substance under investigation and to the measurement fluid inside the measurement chamber. One possible optical measurement is a photometrical method. Photometrical methods feature a higher sensitivity than other methods, a general simplicity and the possibility for large tests series under standardized conditions. For a quantitative analysis by absorption photometry it is common to use e. g. ultraviolet or visible radiation. This spectral range is matching the change of energy of the valence electrons. It is also possible the use the infrared spectral range, at which the molecules of the substance under investigation show a shift in their atomic core oscillation energies.

However, only a small set of substances have absorption bands at light in the visible (color) or ultra-violet range. Nevertheless, in most cases one can transform the substance by means of a chemical reaction to a compound having a characteristic absorption band and detect the concentration of this compound. Since the introduction of photometrical methods, more than 1000 different analysis methods have been described, which all can be used here. The chemical reaction can be initialized by the substance which is diffusing into the measurement chamber. For example it is possible to identify substances such as acetone bodies, bilirubin, cholesterol, iron, bile acid, hemoglobin, uric acid, carbonmonoxide, remaining nitrogen in blood, etc. after suitable conditioning.

The measurement fluid inside the measurement chamber to be used can, therefore depend on the substance under investigation and/or on the matrix. In particular it can be chosen to contain the substance under investigation in a nominal concentration. In this case, the receiver signal shows the difference to the nominal concentration.

A possible measurement principle is to analyze the attenuation of the beam while passing through the measurement fluid, wherein it is also possible to use a wavelength or polarization selective method. It is also possible to use several optical beams of different wavelengths. It is of advantage that the transmitter unit comprises a light source and further an optical filter system or an optical projection system or both. A projection system ensures an optimal transmission through the measurement chamber and adapts the light beam emitted by the source to the diameter of the measurement chamber. It is possible for instance to use a collimation optics. The light source can be a light emitting diode, a laser diode or an array of light emitting diodes.

A filter system is adapted to the optical effect used for measurement, for instance comprise broad-band absorption, wave-length selective absorption, polarization dependent absorption or rotation of polarization. Thus, it is of advantage to use a filter system with contains of a polarization filter and/or an interference filter and/or an edge filter.

A high measurement accuracy is reached, if the detection performs a differential analysis or evaluates two different optical effects. It is therefore of advantage that the receiver unit comprises at least two photo detectors and at least one optical filter system, which is adapted to a filter system at the transmitter.

As already explained, the measurement fluid is chosen to match the requirements of the matrix. In case of biological substances, it is preferred to use physiological sodium chloride solution or glucose solution. If a rotation of polarization is detected it is of advantage that the filter system of the transmitter comprises a polarization filter, that the filter system of the detector also comprises a polarization filter and that the analyzing electronics determines the rotation of polarization of a light beam passing through the measurement chamber filled with the measurement fluid and further determines the concentration of the substance therefrom.

Of course, all features described below and above can be used not only in the combinations mentioned, but also as individual methods and concepts within the scope of this invention.

Figure 2:
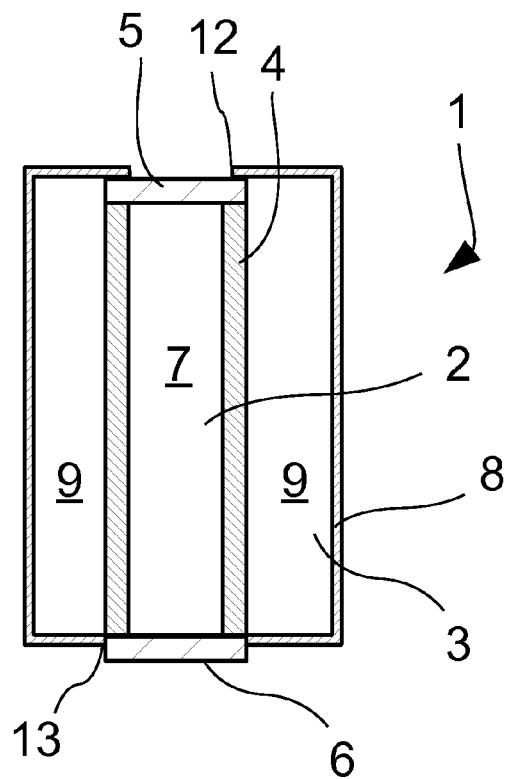
Figure 3:
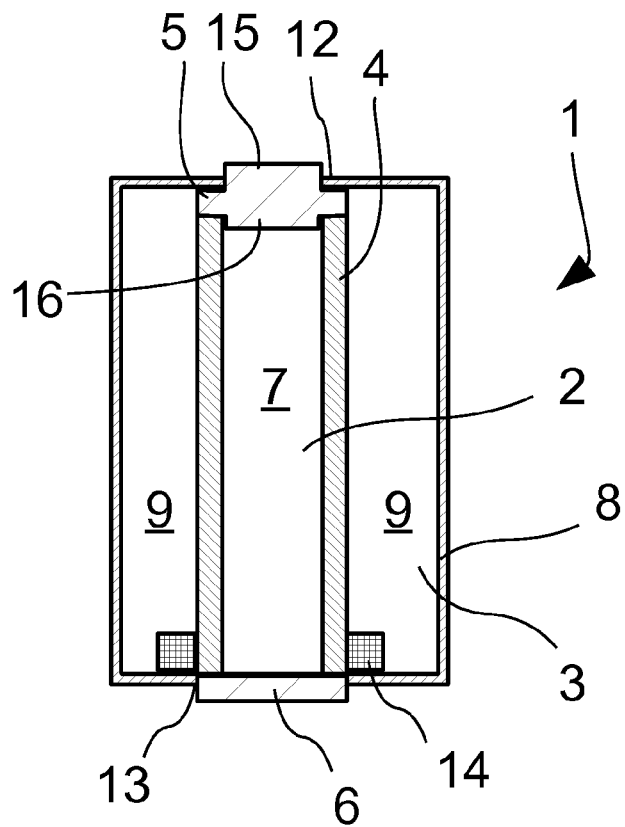
Figure 4:
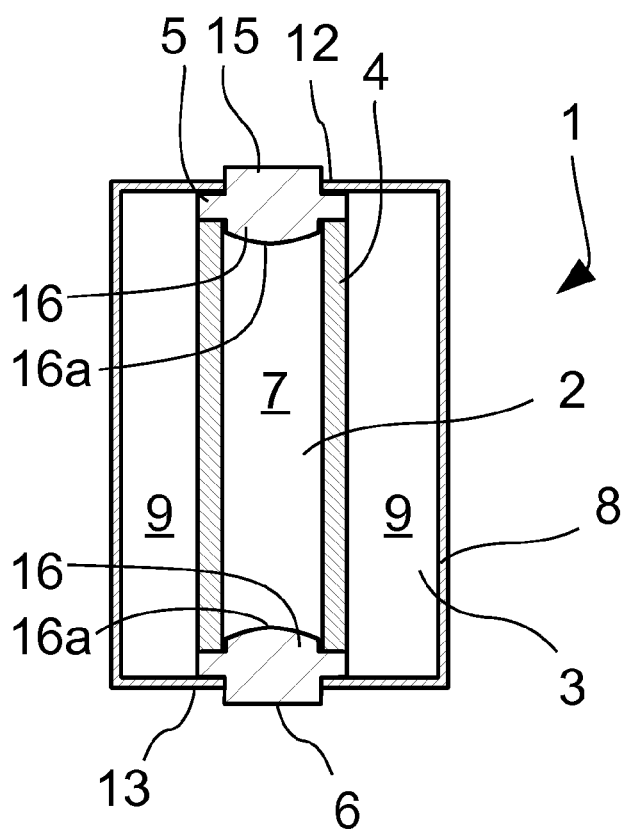
Figure 5:
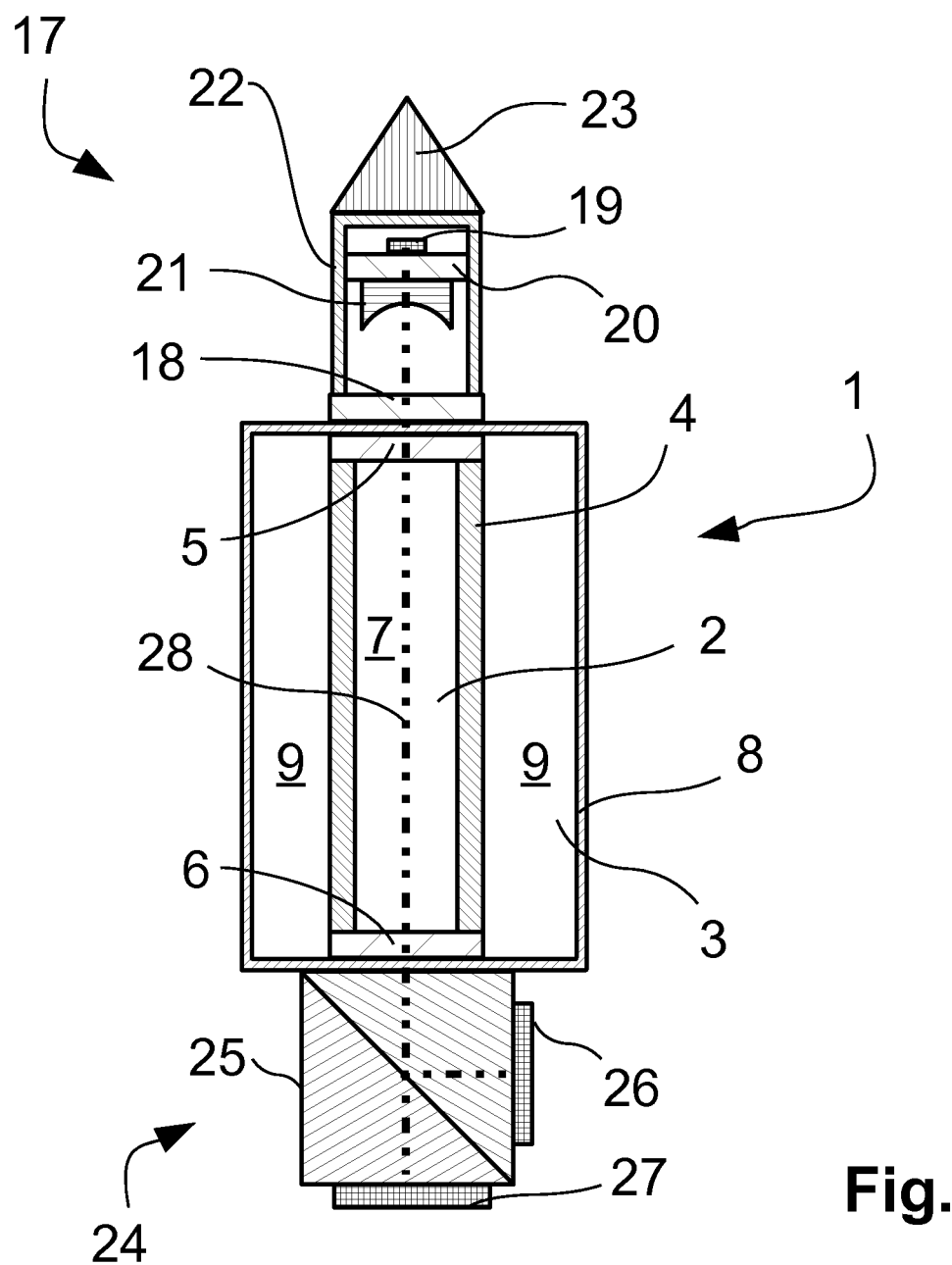
Figure 6:
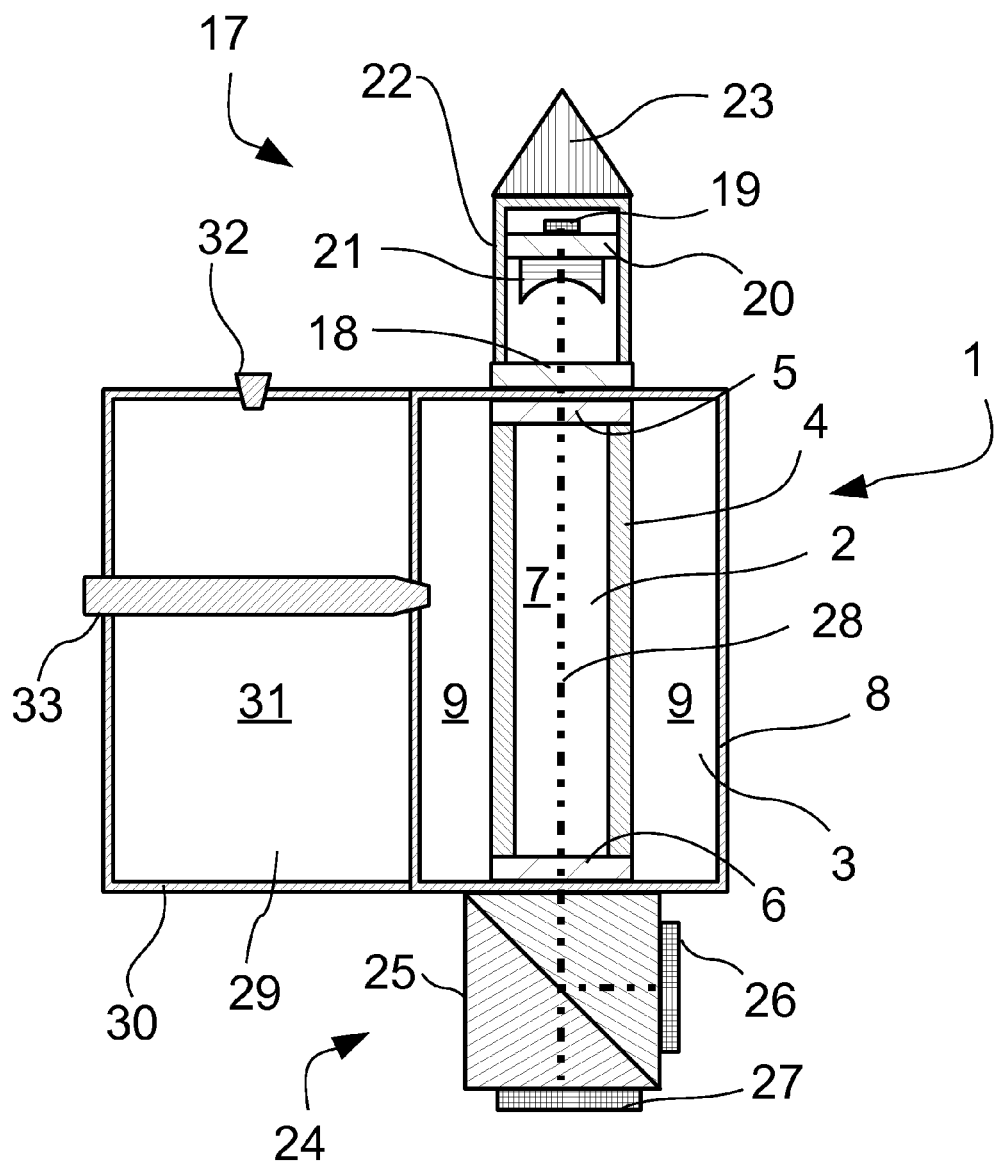
Figure 7:
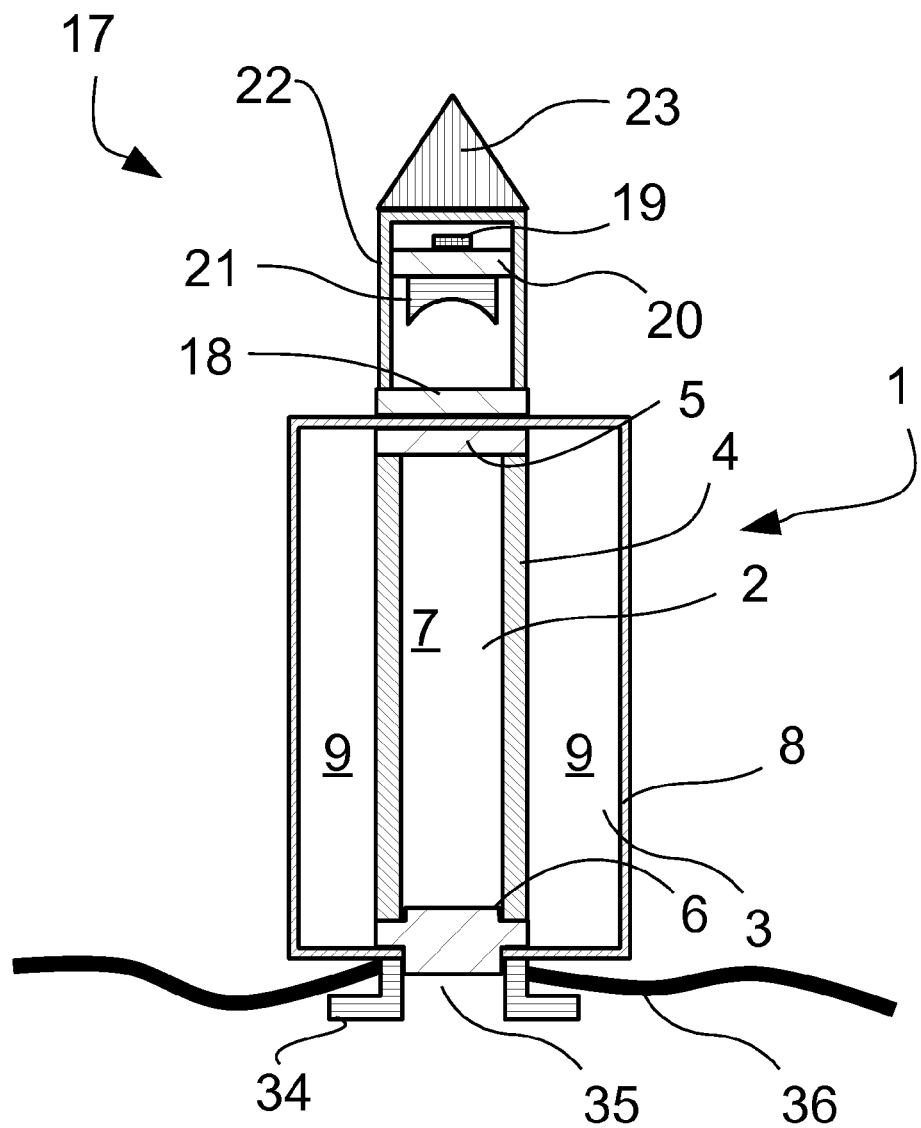
Figure 8:
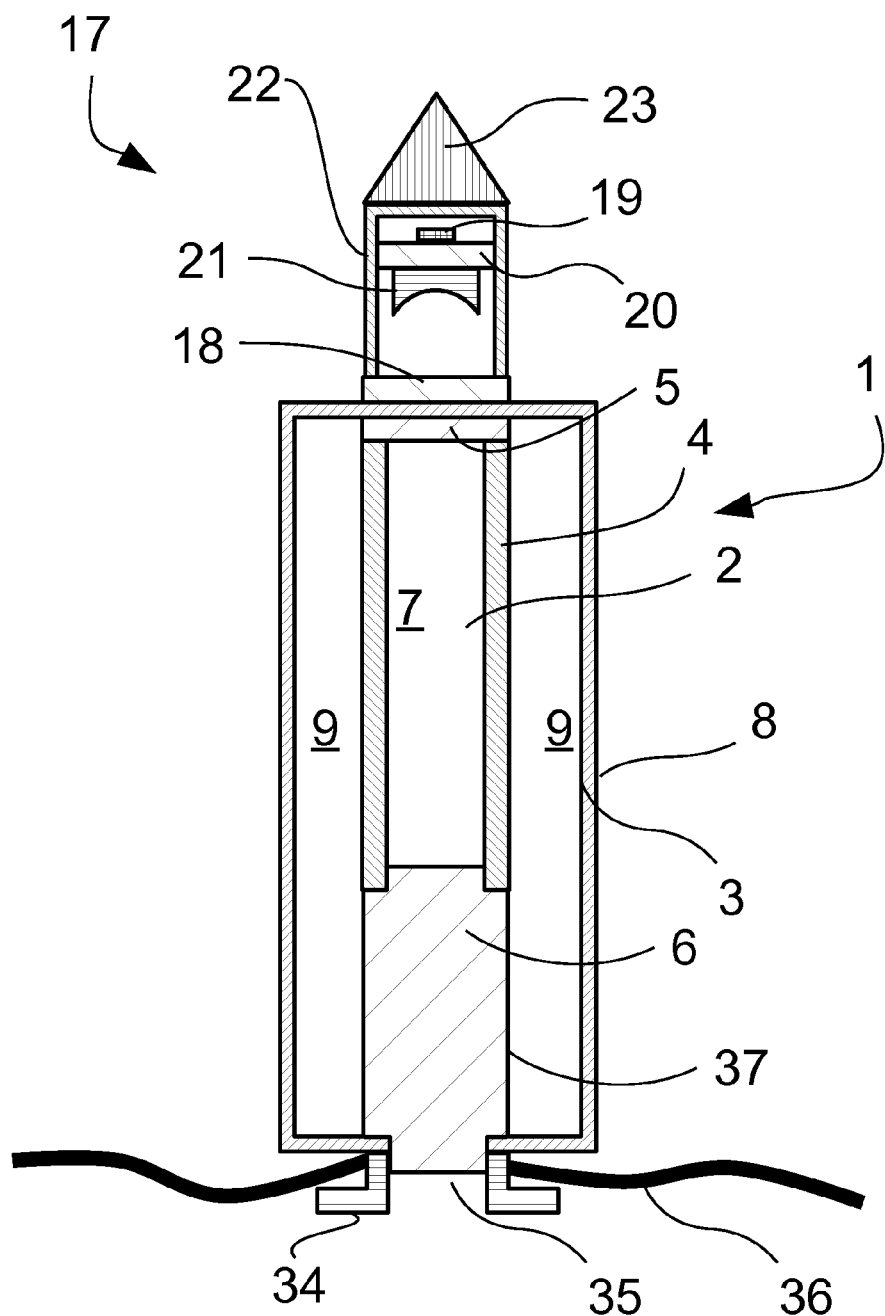
Figure 9:
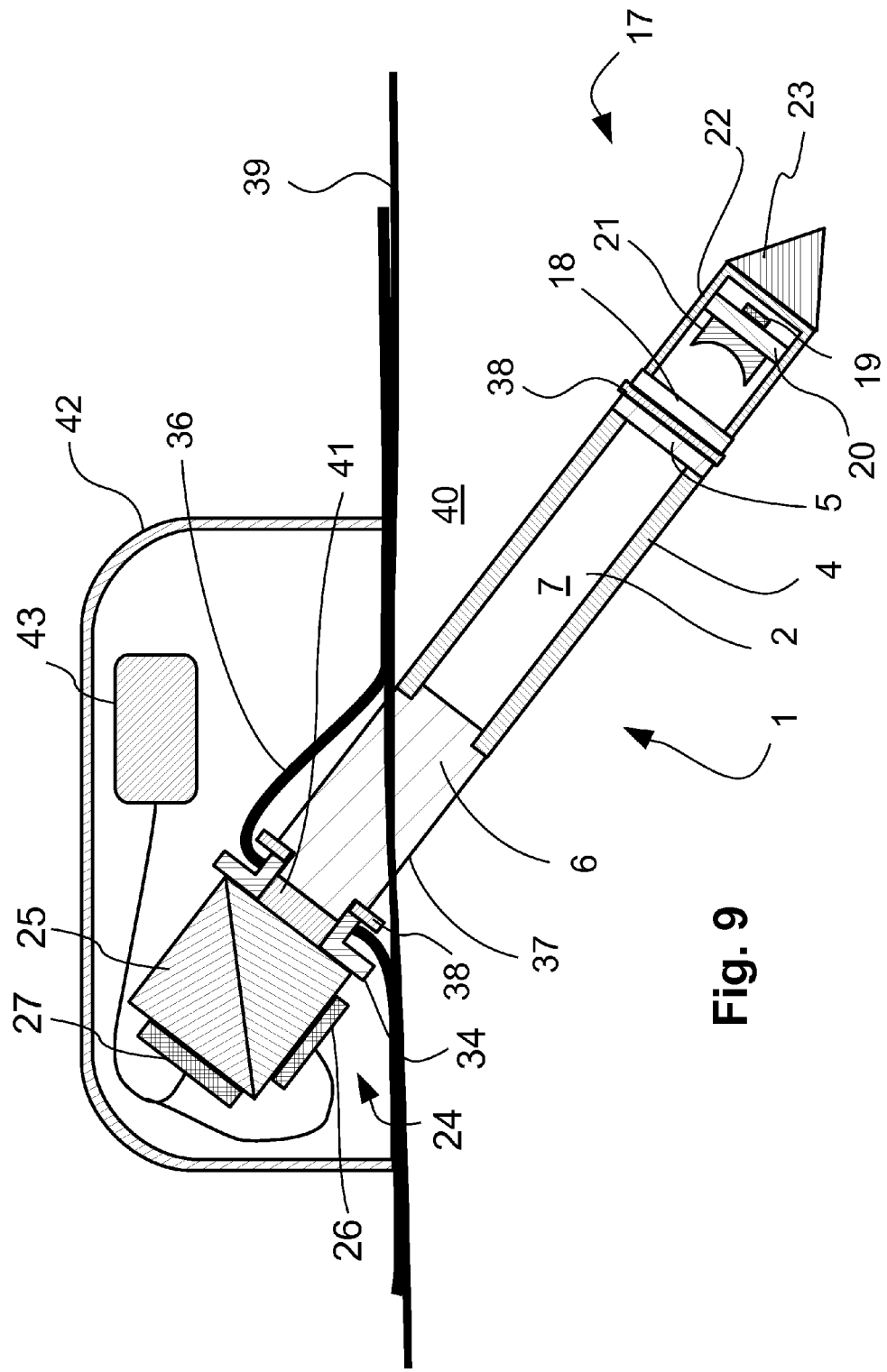

Embodiments of the invention are described further in conjunction with the attached drawings, which shows features related to the invention. In the drawings show:

FIG. 1 a sketch of a measurement chamber device of a sensor for measuring the concentration of a substance within a fluid, FIG. 2-4 modifications of the embodiment of FIG. 1, FIG. 5 a sensor including the measurement chamber device of FIG. 1 in a condition for storage and not yet prepared for penetration of the patient, FIG. 6 a drawing similar to FIG. 5, including a improvement provided for two-point calibration, FIG. 7 a module for a sensor similar to the one of FIG. 1, but without receiver unit, FIG. 8 a modified construction of the module of FIG. 7, and FIG. 9 a schematic drawing of a sensor using the module shown in FIG. 8, which is inserted under the skin of a patient and completed by additional parts.

FIG. 1 shows a schematic cross-section of a measurement chamber device 1 for a sensor, which realizes the measurement principle according to DE 102007031284 A1. In difference to the sensor described there, a modular version of the sensor is provided, which comprises the measurement chamber device 1 and a transmitter unit and a receiver unit to be described later. Regarding the measurement principle DE 102007031284 A1 is fully incorporated by reference.

The measurement chamber device 1 comprises a measurement chamber 2, which is filled by the measurement fluid (for instance saline solution). The measurement chamber is enclosed by a sterilization envelope 3, which is filled also with the measurement fluid. The measurement chamber 2 is formed by a long tube, e. g. a capillary tube 4, and is terminated by windows on both ends 5 and 6. This defines a measurement chamber volume 7, which encloses the measurement fluid leakproof. The term "leakproof" describes the fact, that the measurement fluid can not flow out of the measurement chamber volume, while a diffusion process through the wall of the tube (e.g of the capillary tube 4) is still possible.

The sterilization envelope 3 envelopes the wall with an envelope wall 8 such, that an envelope volume 9 exists between the capillary tube 4 and the envelope wall 8 of the envelope. This envelope volume is also filled with the measurement fluid.

The envelope wall 8 is formed such that it overlap the windows 6 and 5 by envelope windows 10 and 11. The windows 5 and 6 as well as the respective envelope windows 10 and 11 are transparent for the optical radiation which shall pass through the measurement chamber volume 7.

The envelope wall 8 and the sterilization 3 envelope have the effect, that the wall of the capillary tube 4 is surrounded by the measurement fluid internally and externally. The measurement chamber volume 7 and the envelope volume 9 are preferably filled in a vacuum assisted process. In such a process, a small opening is provided in the envelope wall 8, and the measurement chamber device 1 is evacuated and filled with the measurement fluid, e.g. saline solution. After the filling has completed, the opening in the envelope wall 8 is sealed. As an alternative a dedicated valve is provided for the filling process.

The measurement chamber device 1 is designed to be connected with a transmitter unit and a receiver unit at the windows 5 and 6. Reference is made to FIG. 5 which shows this configuration and which will be referred to later in this description of the apparatus. It is essential for the embodiment of FIG. 1, that the envelope wall 8 does not block the windows 5 and 6. The envelope comprises the corresponding envelope windows 11 and 10 for this reason. This allows to attach the optical transmitter unit and the optical receiver unit directly to the envelope windows 11 and 10.

FIG. 2 shows a variation of this concept. It recesses window 5 from the envelope wall 8, which comprises a envelope edge 13 attached to the edge of the window 5. FIG. 2 shows another optional embodiment at the window 6. Here the envelope edge 13 is attached to a side-edge of the window 6.

Another option, which is not illustrated, realizes the window 5 and 6 as optical fiber couplers, which are connected to the transmitter unit or to the receiver unit. In this case, the envelope wall 8 is attached to the fiber coupler. The fiber coupler is installed at the outer face of the window. This particular implementation is an option for all configurations described below and above.

FIG. 3 shows two further options for mounting or providing of the sterilization envelope 3 in the region of the windows 5 and 6. At the window 6, a attachment ring 14 is provided, which is mounted to the surface of the capillary tube, to enable a better attachment of the envelope edge 13. Of course, the attachment ring 14 can equally be provided at the periphery of the window 5. The attachment ring provides a surface for attaching the envelope edge 13.

FIG. 3 shows further, that the window 5 is equipped with an outside nose 15, which is oriented toward the outside of the measurement chamber. This results in a ring notch or recess at the window 5, where the envelope edge 13 is mounted.

Attachment of the envelope wall 8 of the sterilization envelope 3 can be realized in any combination according to the construction concepts shown in FIG. 1 and FIG. 3. Other types of attachment to the edge of the windows are possible, too.

FIG. 3 shows an additional and optional feature for one of the windows, in the example shown for the window 5. It has an additional internal projection 16, which is pointing to the inside of the measurement chamber 7 in the region of the end of the capillary tube 4, more precisely in the area where the window 5 is mounted to the front side of the capillary tube 4. If an adhesive bond is used to mount the window to the front side of the capillary tube, the diffusion properties of the capillary tube 4 are influenced near this front side. To prevent that this influence affects the diffusion into the measurement chamber volume 7, the internal projection 16 provides for the measurement chamber 2 having no volume 7 at the area where the diffusion properties are influenced and, therefore, no volume for the measurement fluid. The internal projection 16 is of advantage independently on the technology for mounting of the envelope wall 8 to the window 5 and 6, of course.

FIG. 4 shows a modified construction of the measurement chamber of FIG. 3. In this case, both windows 5 and 6 are equipped with internal projections 16. Such windows are in further modification of the construction of FIG. 3 also equipped with a convex surface 16a pointing to the measurement chamber volume 7. This convex surface 16a pushes possible residual bubbles in the measurement chamber 7 to the periphery and therefore prevents any disturbance of the optical transmission. Furthermore, the convex surfaces 16a are designed such that the difference in refraction index between the material of the window 5, 6 and the measurement fluid results in an improvement of the optical properties in terms of a better focus of the beam and/or a reduction of interfering edge effects.

The sterilization envelope 3 enables a sterilization of the measurement chamber device by ionizing radiation, wherein transmitter unit and receiver unit, which will be described later, are not exposed to the ionizing radiation, too. Prior to employing the sensor with the measurement chamber device 1, the sterilization envelope 3 is removed. To assist this, a pull-thread or a breaking-line can be provided in the envelope wall 8. It is also possible to design the bounds at the cover edge 12 or 13 to notch at certain pulling force.

The wall of the measurement chamber 2 enables diffusion permeation of substances between the surrounding matrix and the measurement fluid in a substance selective and bidirectional way. The selection is chosen such that only the substance to be detected can diffuse through the wall of the measurement chamber 2, or has at least a diffusion coefficient of one order of magnitude higher than other substances in the matrix.

Substances with a size smaller than a maximal size can diffuse through the wall and into the volume of the measurement chamber 2. Substances which are larger in size cannot pass. A typical value for the maximal size is e. g. 30 kDalton. In case of a wall size selectivity obtained by treatment or forming of the wall, glucose can diffuse into the measurement chamber, but larger substances which may have a more significant impact on the measurement yet to be described are blocked from entering.

The measurement chamber device 1 causes a dynamic and defined substance selectivity.

FIG. 5 shows a scheme of the measurement chamber device 1 complemented by the transmitter unit 17 and the receiver unit 24. The transmitter device 14 comprises a window 18, which transmits optical radiation from a light source, for example a light emitting diode 19, to be coupled out at the window 18. The diode 19 is mounted on a printed circuit board 20 which also carries optics 21 to suitably focus the light beam of the diode 19. A housing 22 supports the board 20 and the diode 19 and has optionally a needle tip 23 attached for better penetration into the skin of a mammal, for instance of a patient where the glucose level in the blood is to be measured. The described configuration of the transmitter unit 17 is an example only. Important is the fact, that the device is adapted to be attached to the window 5. The attachment to the window 5 is realized in the embodiment of FIG. 5, in that the windows 18 and 5 are connected optically in an adequate way. If the already mentioned transmitter unit 17, which is connected with the measurement chamber device 1 via an optical fiber is used, the window 18 is replaced by a fiber coupler and an optical fiber runs to the window 5 which is also provided in form of a fiber coupler.

To simplify the drawing, FIG. 5 shows a measurement chamber device 1 according to FIG. 1. The other embodiments of the measurement chamber device 1 can equally be used, wherein the transmitter unit 17 is designed appropriate for the respective design of the window 5 (or fiber coupler).

The receiver unit 24 is provided at the opposing window 6. It comprises a beam splitter cube 25, which splits the optical radiation passed through the measurement chamber 2 to feed two detectors 26 and 27. The splitting is realized according to the measurement principle, e.g. polarization analysis, spectral analysis etc. All options explained for the transmitter unit 17 and the window 5 can equally be used for the connection between the receiver unit 24 and the window 6. It is also possible, to mount the beam splitter cube or an element optically bonded thereto directly to the window 6. As an alternative, a fiber optical connection can be used by providing the window 6 as a fiber coupler which is connected by an optical fiber to a fiber coupler at the receiver unit 24.

The terms "mounting" or "attachment" of the transmitter or receiver units 17, 24 to the measurement chamber device 1 used above or below apply in the same sense to embodiments based on a fiber optical connection between the transmitter unit 17 and the measurement chamber device 1 and between the receiver unit 24 and the measurement chamber device 1.

The optical beam 28 emitted by the diode 19 is conditioned in an adequate way (for instance by the optics 21) and is, after passing through the measurement chamber 2 and interacting with the substances in the chamber, directly measured by the receiver device 24. In case of the realization shown in FIG. 5, the attenuation of the beam depends on the polarization dependent absorption within the measurement fluid. This absorption is related to the concentration of the substance, which gives, based on the intensity of the optical beam at the detectors 26, 27 and the signal amplitude of the detected signals automatically an indication of the concentration of the substance. The construction of FIG. 5 is most suitable for substances influencing the absorption.

The transmitter unit 17 and the receiver unit 24 are both connected to a control electronics (not shown), which controls the diode 19 at the one side and reads out the signals of the two detectors 26, 27 at the other side.

FIG. 5 shows a sensor under storage conditions. Before piercing the patient with the sensor, the sterilization envelope or its envelope wall 8 is removed.

In the fabrication process the measurement chamber device 18 is already aseptic in its interior at the time when the transmitter device 17 and the receiver device 24 are mounted to the measurement chamber device 1, because of sterilization with ionized radiation. The sensor of FIG. 5 can also be sterilized by means of simple surface sterilization, e. g. by a so called chemical gas sterilization, once the transmitter unit 17 and the receiver unit 24 have been mounted.

The optics 21, which is shown for the transmitter device 17, is shown as collimator optics just by way of example. It may further comprise a filter system such as polarization filter, interference filter or edge filter additionally or alternatively. The features of the optical filter system depend on the measurement method applied. It is preferred of course that the receiver unit 24 comprises a receiver filter system matching the properties of the filter system of the transmission unit. This allows a measurement method going beyond the polarimetrical differential measurement mode realized by the set-up of FIG. 5.

FIG. 6 shows a sensor having an improved measurement chamber device 1. It includes additionally a calibration chamber 29, which is realized for example by an shell wall 30, which is attached to the envelope wall 8 of the sterilization envelope 3. The calibration chamber 29 provides a calibration volume 31, which is filled with a calibration substance. The calibration volume 31 is on the one hand filled via a fluid connection 32. This may be the same type of filling as described earlier for the measurement chamber 2 and the sterilization envelope 9. On the other hand, a fluid connection 33 is provided between the calibration volume of the calibration chamber 29 and the envelope volume 9 of the sterilization envelope. This connection can be opened selectively, to enable mixing of the calibration fluid in the calibration volume 31 with the measurement fluid in the envelope volume 9. This allows to obtain a second measurement point for calibration of the sensor as already explained in the general part of this specification. For calibration the sensor is first operated without connecting the two fluids. The measurement fluid in the measurement volume 7 including the concentration of the substance under investigation contained therein is measured first for obtaining a first calibration point. In a further step the fluid connection 33 is established, e. g. opened, and the calibration fluid from the calibration volume 31 and the measurement fluid from the chamber volume 9 mix. Due to the diffusion properties of the capillary tube 4 the composition of the substances inside the measurement volume 7 changes. This provides a second calibration point.

The calibration chamber 29 is shown in FIG. 6 to be directly connected to the sterilization envelope 3, i. e. the calibration chamber 29 and the sterilization envelope 3 share a common wall. This is an option, but not mandatory. The calibration cover 29 can equally be an independent shell enclosing the calibration fluid. It is important that the fluid connection can be established between the calibration chamber 29 and the sterilization envelope 3 and that calibration fluid and measurement fluid can mix through such connection.

This fluid connection can also be realized by a piercing port in the sterilization envelope 3, wherein the calibration chamber can be realized by a needle and syringe containing the calibration fluid.

FIG. 7 shows a schematic drawing of the module for a sensor for measuring the concentration of a substance, which operates according to the described principles. The module consists of the measurement chamber device 1 and the transmitter unit 17, which are designed according to the described concepts. For attachment of the transmitter unit 24 a flange 34 is provided at the corresponding window 6 to mount the transmitter unit 24. To realize a good transmission of optical radiation from the window 6 to the receiver unit 24, the flange 34 comprises a volume 35 into which an immersion fluid, for instance immersion oil, can be filled before the receiver unit 24 and the flange 34 are mounted to each other.

Use and realization of a flange is just an example for a connection piece to mount the receiver unit 24. An important aspect of the construction in FIG. 7 is to provide a module that includes all components which will later be inserted in the body, at least in part, where the substance under investigation is to be analyzed. The connection piece, e. g. in form of the flange 34, allows a simple mounting of the components, i. e. the receiver unit 24, which are not to be incorporated the body. The module achieves a cost-efficient permanent operation, because only the module needs to be replaced, but not the receiver unit 24.

For fixating of the sensor after insertion of the module into the body a mounting and protection device, for instance in the form of a collar 36, is provided at the window 6. The mounting and protection device is on one end rigidly mounted to the module and is flexible on the other end. It can be fixated to the skin of the body where the module is inserted, for instance by a suture, adhesive or a patch. This enables on the one hand that the inserted module can follow the movements of the body, which results in a low stress for the patient.

On the other hand it protects the inserted module and the penetration point of the skin against infections. The mounting and protection device, e. g. the collar 36, is preferred to be not transparent to optical radiation such that no interfering radiation can reach the receiver unit 24 laterally along the measurement device 1. It also prevents interfering optical radiation bypassing through the skin and generating an interfering signal at the receiver unit 24.

FIG. 8 shows a modification of the measurement chamber device 1—as an example it is based on the module shown in FIG. 7. The window 6 for connecting the receiver unit 24 is equipped with an extension 36. This ensures that the capillary tube 4 is in a region of the body where interstitial fluid exists, even at significantly tilted penetrations of the module or the sensor. This is illustrated by FIG. 9, which shows the sensor to be pierced in underneath skin 39 in tilted manner. Prior to piercing, the envelope wall 8 of the sterilization envelope 3 was removed, of course. Depending on the mounting of the envelope wall 8 in the area of the windows 5 and 6 an envelope leftover 38 can remain, which is indicated in FIG. 9 as an example, which even leaves an envelope window at the window 5 in the optical path, but this particular leftover does not disturb operation.

FIG. 9 shows further the receiver unit 24 attached to the flange 34. In this particular case there an immersion fluid 41 was introduced between the receiver unit 24 and the window 6, which ensures a quite complete transmission of the radiation from the window 6 to the receiver unit 24. The receiver unit 24, for example the detectors 26 and 27 are connected to electronics 34, which processes the suitable signal readout.

The sensor is attached to the skin 39 by the collar 36. The flexibility of the collar 36 lets the sensor inserted into the skin follow the movement of the human body. At the same time, the part of the sensor which is sticking out of the skin is covered by a protective cap 42, which is attached to the skin 39 independently to the collar 36. The electronics 43 is mounted to the protective cap 42, and the connection between the electronics 43 and the receiver or transmitter unit 24, 17 are flexible. This ensures that any pressure to the protection cap 42 does not cause movement of inserted parts of the sensor. At the same time the protective cap 32 protects sensors parts sticking out and holds the electronics 34.

To change the sensor parts penetrating the body, which is typically needed after 14 days, the protective cap 42 is removed by disconnecting electrical connectors to the sensor. Then, the connection between the receiver unit 24 and window 6 is unfastened. Then, the module consisting of the measurement chamber device 1 and the receiver unit can be extracted from the body and a fresh module can be inserted, to which the receiver unit 23 is re-connected. This realizes a cost efficient renewal of the sensor without need to replace the receiver unit 24.

The invention claimed is:

1. A measurement chamber device for an optical sensor for measuring the concentration of a substance in the interstitial liquid of a mammal, wherein the measurement chamber device comprises:
a measurement chamber, wherein the measurement chamber is filled with a measurement liquid and comprises a wall, the wall including at least one wall section enabling a better diffusion of the substance than of other components of the interstitial liquid, the measurement chamber, further including a first measurement chamber window section receiving a transmitter unit for emitting optical radiation into the measurement chamber and a second measurement chamber window section receiving a receiver unit for detecting optical radiation transmitted through the measurement chamber, the measurement chamber device further comprising a sterilization envelope which encloses the wall section of the measurement chamber but does not block the optical radiation at the measurement chamber window sections, the sterilization envelope defining a pair of openings in opposing walls thereof corresponding to the measurement chamber windows, wherein each of the pair of openings is sealingly coupled to the measurement chamber around the first measurement chamber window section and the second measurement chamber window section, respectively, wherein the sterilization envelope is filled with measurement liquid to bathe the wall section in measurement liquid, and wherein the sterilization envelope is selectively removable before use of the measurement chamber.

2. The measurement chamber device of claim 1, wherein the sterilization envelope comprises a sheet having an opening thread to remove the enclosing envelope.

3. The measurement chamber device of claim 1, wherein the measurement chamber window sections are glued to the wall and extend into the measurement chamber and cover sections of the wall, at which sections a diffusion permeability of the wall is reduced due to the gluing.

4. The measurement chamber device of claim 1, wherein a mounting portion is provided proximate at least one of the first measurement chamber window section or the second measurement chamber section to mount either the transmitter unit or the receiver unit, wherein the at least one mounting portion includes a flange.

5. The measurement chamber device of claim 4, wherein the at least one mounting portion provides a reservoir for an immersion liquid.

6. The measurement chamber device of claim 1, wherein a calibration chamber is provided which contains a calibration liquid and is connected to the sterilization envelope via a liquid connection, wherein the liquid connection is closed initially and can be opened for calibration purposes to mix the measurement liquid with the calibration liquid.

7. The measurement chamber device of claim 1, wherein a mounting and protection device is attached to the first measurement window section.

8. The measurement chamber device of claim 7, wherein the mounting and protection device is an elastic sleeve.

9. The measurement chamber device of claim 7, wherein the mounting and protection device of the measurement chamber device comprises an optically non-transparent material to prevent penetration of interfering light.

10. The measurement chamber device of claim 1, wherein a mounting and protection device is attached to the second measurement window section.

11. The measurement chamber device of claim 1, wherein at least one of the first and second measurement window section comprises a window surface having a convex form at the inside of the measurement chamber to push any gas bubbles in the measurement liquid to the periphery of the measurement chamber window section.

12. The measurement chamber device of claim 1, wherein the first measurement window section is a fiber coupler to connect the transmitter unit by an optical fiber.

13. The measurement chamber device of claim 1, wherein the second measurement window section is a fiber coupler to connect the receiver unit by an optical fiber.

14. The measurement chamber device of claim 1, wherein the sterilization envelope is sealingly coupled to a periphery of the measurement chamber window sections around each of the pair of openings.

15. A module for a sensor for measuring a concentration of a substance, the module comprising a measurement chamber device including a measurement chamber and filled with a measurement liquid, the chamber comprising a wall including at least one wall section enabling a better diffusion of the substance than of other components of the interstitial liquid, the measurement chamber device further comprising a first measurement chamber window section designed to be connected to a transmitter unit for emitting optical radiation into the measurement chamber and a second measurement chamber window section designed to be connected to a receiver unit for detecting optical radiation transmitted through the measurement chamber, wherein the wall and the measurement window sections enclose the measurement liquid, and the device further comprising a sterilization envelope enclosing the wall section of the measurement chamber, wherein the sterilization envelope is filled also with measurement liquid to bathe the wall section in measurement liquid, and wherein the measurement chamber is elongated having a length and a pair of opposing ends, the first measurement chamber window section being located at one end and the second measurement chamber window section being located at the opposing end, the measurement chamber being adapted for transmission of the optical radiation along the length without reflection, the sterilization envelope defining a pair of openings in opposing walls thereof corresponding to the measurement chamber window sections, wherein each of the pair of openings is sealingly coupled to the measurement chamber around the first measurement chamber window section and the second measurement chamber window section respectively.

16. A sensor for measuring a concentration of a substance, the sensor comprising a transmitter unit for emitting optical radiation, a receiver unit for receiving the optical radiation, and a measurement chamber device, the measurement chamber device comprising a measurement chamber and filled with a measurement liquid, the measurement chamber comprising a wall including at least one wall section enabling a better diffusion of the substance than of other components of the interstitial liquid, the measurement chamber further comprising a first measurement chamber window section adapted to receive the transmitter unit, and a second measurement chamber window section receiving the receiver unit, wherein the wall and the measurement window sections enclose the measurement liquid, the measurement chamber device further comprising a sterilization envelope enclosing the wall section of the measurement chamber, the sterilization envelope being filled with measurement liquid to bathe the wall section in measurement liquid, and being selectively removable before use of the measurement chamber, the sterilization envelope defining a pair of openings in opposing walls thereof corresponding to the measurement chamber window sections, wherein each of the pair of openings is sealingly coupled to the measurement chamber around the first measurement chamber window section and the second measurement chamber window section, respectively.

17. The sensor of claim 16, comprising a protection cap to be placed over the receiver unit, the protection cap comprising a flexible portion to connect to the receiver unit.

18. The sensor of claim 17, wherein the protection cap is adapted to be attached independently from the measurement chamber device.

19. The sensor of claim 17, wherein the protection cap comprises an optically non-transparent material to prevent penetration of interfering light.

20. A method for producing a measurement chamber device, the measurement chamber device comprising a measurement chamber having a wall with at least one wall section enabling better diffusion of a substance contained in interstitial liquid than of other substances contained in the interstitial liquid, the measurement chamber further having a first measurement chamber window section and a second measurement chamber window section, the measurement chamber device further including a sterilization envelope enclosing the wall section of the measurement chamber, the sterilization envelope defining a pair of openings in opposing walls thereof corresponding to the measurement chamber windows, each of the pair of openings being sealingly coupled to the measurement chamber around the first measurement chamber window section and the second measurement chamber window section, respectively, the method comprising:
   a) enclosing the measurement chamber in the sterilization envelope;
   b) filling the measurement chamber and sterilization envelope with the measurement liquid under vacuum conditions and closing a port in the sterilization envelope; and
   c) sterilizing the filled unit with ionizing radiation.

21. A method for producing a module for a sensor for measuring a concentration of a substance, the module comprising a measurement chamber device including a measurement chamber, the chamber comprising a wall including at least one wall section enabling a better diffusion of the substance in the interstitial liquid than of other components of the interstitial liquid, the measurement chamber device further comprising a first measurement chamber window section designed to be connected to a transmitter unit for emitting optical radiation into the measurement chamber and a second measurement chamber window section designed to be connected to a receiver unit for detecting optical radiation transmitted through the measurement chamber, the device further comprising a sterilization envelope enclosing the wall section of the measurement chamber, the measurement chamber being elongated having a length and a pair of opposing ends, the first measurement chamber window section being located at one end and the second measurement chamber window section being located at the opposing end, the sterilization envelope defining a pair of openings in opposing walls thereof corresponding to the measurement chamber window sections, wherein each of the pair of openings is sealingly coupled to the measurement chamber around the first measurement chamber window section and the second measurement chamber window section, respectively, the method comprising:
   a) enclosing the measurement chamber in the sterilization envelope;
   b) filling the measurement chamber and sterilization envelope with the measurement liquid under vacuum conditions and closing a port in the sterilization envelope;
   c) sterilizing the measurement chamber and sterilization envelope with ionizing radiation; and
   d) connecting the transmitter unit to the measurement window section, and sterilizing the transmitter unit by surface sterilization.

22. A method for producing a sensor for measuring a concentration of a substance, the sensor comprising a transmitter unit for emitting optical radiation, a receiver unit for receiving the optical radiation, and a measurement chamber device, the measurement chamber device comprising a measurement chamber and filled with a measurement liquid, the measurement chamber comprising a wall including at least one wall section enabling a better diffusion of the substance than of other components of the interstitial liquid, the measurement chamber further comprising a first measurement chamber window section adapted to receive the transmitter unit, and a second measurement chamber window section receiving the receiver unit, the measurement chamber device further comprising a sterilization envelope enclosing the wall section of the measurement chamber, the sterilization envelope being selectively removable before use of the measurement chamber, the sterilization envelope defining a pair of openings in opposing walls thereof corresponding to the measurement chamber window sections, wherein each of the pair of openings is sealingly coupled to the measurement chamber around the first measurement chamber window section and the second measurement chamber window section, respectively, the method comprising:
   a) enclosing the measurement chamber in the sterilization envelope;
   b) connecting a calibration chamber containing a calibration liquid to the sterilization envelope via a liquid connection, the liquid connection being selectively openable and closable;
   c) filling the measurement chamber and sterilization envelope with the measurement liquid under vacuum conditions and closing a port in the sterilization envelope;
   d) sterilizing the measurement chamber and sterilization envelope with ionizing radiation;
   e) connecting the receiver unit to the second measurement chamber window section and connecting the transmitter unit to the first measurement window section; and
   f) calibrating the sensor by performing a first measurement with the liquid connection closed, subsequently opening the liquid connection to mix the measurement liquid with the calibration liquid, and performing a second measurement with the measurement liquid being mixed with the calibration liquid.

\* \* \* \* \*